United States Patent [19]

Rose et al.

[11] Patent Number: 4,832,697

[45] Date of Patent: * May 23, 1989

[54] HAIR DYE PREPARATIONS CONTAINING SUBSTANTIVE NITRODIPHENYLAMINE DERIVATIVES

[75] Inventors: David Rose, Hilden; Edgar Lieske, Duesseldorf; Norbert Maak, Neuss, all of Fed. Rep. of Germany

[73] Assignee: Henkel Kommanditgesellschaft auf Aktien, Duesseldorf, Fed. Rep. of Germany

[*] Notice: The portion of the term of this patent subsequent to Jul. 12, 2005 has been disclaimed.

[21] Appl. No.: 160,965

[22] Filed: Feb. 26, 1988

[30] Foreign Application Priority Data

Feb. 26, 1987 [DE] Fed. Rep. of Germany ....... 3706224

[51] Int. Cl.⁴ .......................... A61K 7/13; C07C 87/54
[52] U.S. Cl. ............................................. 8/429; 8/407;
  8/414; 260/505; 260/509; 260/510; 562/433;
  562/434; 562/435; 564/433; 564/434
[58] Field of Search .................. 8/429, 407, 423, 424;
  564/433, 434; 562/433, 434, 435; 260/508, 509, 510

[56] References Cited

U.S. PATENT DOCUMENTS 2,611,785  9/1952  Gunther .............................. 260/509
4,029,815  6/1977  Sherlock et al. .................... 424/309
4,257,977  3/1981  Yelland .............................. 260/510

FOREIGN PATENT DOCUMENTS 2830497  1/1980  Fed. Rep. of Germany .
 600640  4/1948  United Kingdom .
 955743  4/1964  United Kingdom ................ 564/434

*Primary Examiner*—Paul Lieberman
*Assistant Examiner*—Linda D. Skaling
*Attorney, Agent, or Firm*—Ernest G. Szoke; Wayne C. Jaeschke; Norvell E. Wisdom, Jr.

[57] ABSTRACT

This invention encompasses compounds of the formula:

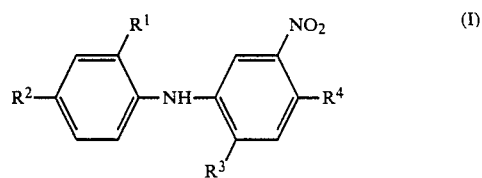

wherein:
  one of $R^1$ or $R^2$ is nitro and the other is —$SO_3H$ or COOH; and
  one of $R^3$ or $R^4$ is hydrogen and the other is —$NR^5R^6$, where $R^5$ and $R^6$ independently are hydrogen, $C_{1-4}$ alkyl, or $C_{2-4}$ hydroxyalkyl;

or a water soluble salt thereof; hair dye preparations containing the above compounds as substantive hair dyes; and methods for dyeing hair using such preparations.

29 Claims, No Drawings

HAIR DYE PREPARATIONS CONTAINING SUBSTANTIVE NITRODIPHENYLAMINE DERIVATIVES

BACKGROUND OF THE INVENTION

1. Field of the Invention

This invention relates to hair dye preparations containing substantive hair dyes as well as some of the dyes per se. Preparations of the type in question contain substantive hair dyes in a cosmetic carrier. In many cases, such preparations additionally contain oxidation dye precursors to produce certain shades. The cosmetic carriers used for the substantive hair dyes and oxidation dye precursors, if any, are creams, emulsions, gels, shampoos, foam aerosols or other preparations suitable for application to the hair.

2. Statement of Related Art

In addition to the oxidation dyes, which are formed by the oxidative coupling of one or more developer components with one or more coupler components, substantive hair dyes play a prominent part in the dyeing of hair. Substantive dyes have the advantage of being used without the addition of oxidizing agents. The substantive dyes used are predominantly nitrobenzene derivatives. They are used either on their own or in combinations with other substantive dyes, cationic azo dyes such as anthraquinone dyes, indophenols, triphenylmethane dyes, or with oxidation dyes.

Good hair-dyeing preparations have to form the required shades with sufficient intensity. They must be readily absorbed by human hair without excessively staining the scalp. The coloring produced with them must show high stability to light, heat, perspiration, shampoos and the chemicals used in the permanent waving of hair. Finally, they should be safe to use from the toxicological and dermatological viewpoint.

Among the substantive nitrobenzene derivatives, the nitroanilines and derivatives thereof play an important part because some of these dyes produce intensive, light-stable colors. However, the known substantive nitroaniline dyes have disadvantages in that, on the one hand, they show only limited solubility in water, which leads to problems during formulation of the hair dye preparations, and on other hand they are not sufficiently fast to washing, i.e. the dye finishes fade considerably after repeated shampooing.

In addition, it is desirable that substantive dyes should be able to produce shades of red to obtain fashionable hair colors. 2-Nitro-p-phenylenediamine and amino-substituted derivatives thereof are normally used for this purpose. Unfortunately, these chemically related compounds are difficult to dissolve and difficult to disperse in water. This readily leads to uneven or to faint hair colors. Moreover, particularly where hair preparations have high concentrations of dye, the dyes crystallize out and are not adsorbed onto the hair to be dyed. Accordingly, there is an urgent need for substantive hair dyes showing improved solubility in water.

Furthermore, substantive hair dyes desirably show high compatibility with other dyes, for example with oxidation dye precursors and with the other components normally used in oxidation hair dye preparations, because substantive dyes and oxidation dyes are often combined with one another for color modification. Accordingly, high stability to reducing agents and oxidizing agents is necessary.

DESCRIPTION OF THE INVENTION

Other than in the operating examples, or where otherwise indicated, all numbers expressing quantities of ingredients or reaction conditions used herein are to be understood as modified in all instances by the term "about".

This invention provides hair dye preparations containing one or more substantive hair dyes, in an aqueous cosmetic carrier, in which the substantive hair dyes are one or more compounds of the formula:

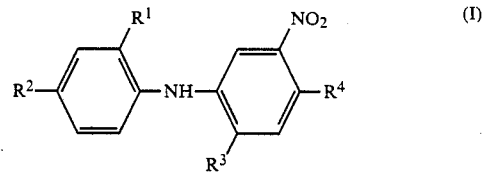

wherein: one of $R^1$ or $R_2$ is nitro while the other is $-SO_3H$ or $'COOH$; and one of $R^3$ or $R_4$ is hydrogen while the other is $-NR_5R_6$, where $R_5$ and $R_6$ independently are hydrogen, $C_{1-4}$ of alkyl or $C_{2-4}$ hydroxyalkyl; as well as the water soluble salts of the above compounds.

Among the compounds corresponding to formula (I), those in which either $R_3$ or $R_4$ is amino or 2-hydroxyalkylamino are particularly preferred.

The dyes corresponding to formula (I) produce orange-yellow to brown colors of high intensity, light stability and fastness to shampooing of the hair.

The dinitrodiphenylamine derivatives corresponding to formula (I) and water-soluble salts thereof are novel and, accordingly, are per se covered by the present invention.

The compounds corresponding to formula (I) are generally prepared by reaction of 4-chloro-3-nitrobenzoic acid, 4-chloro-3-nitrobenzenesulfonic acid, 2-chloro-5-nitrobenzoic acid or 2-chloro-5-nitrobenzenesulfic acid with a nitroaniline corresponding to the following formula

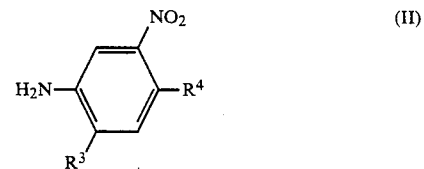

in which $R_3$ and $R_4$ are as defined for formula (I), with the elimination of HCl in the presence of a base, for example an alkali carbonate.

In the context of the invention, water soluble salts are primarily understood to be the salts of strong bases, including: alkali salts, such as sodium or potassium, ammonium salts, $C_{2-4}$ alkanolammonium salts such as monoethanolammonium, triethanolammonium, or isopropanolammonium, sodium being preferred.

The hair dye preparations according to the invention may contain the (first) substantive nitrodiphenylamine derivatives corresponding to formula (I) either alone or in combination with known other (second) substantive dyes, for example with other nitrobenzene derivatives, anthraquinone dyes, triphenylmethane dyes or azo dyes. When present, the second substantive hair dyes are in any amount effective to alter the color of hair to be treated to a desired degree. In a further invention embodiment, the substantive dyes of general formula (I), by virtue of their high resistance to reducing agents and oxidizing agents, are also eminently suitable for combination with oxidation hair dye precursors, i.e. for modifying the shades of oxidation hair dye preparations. Oxidation hair dye preparations contain as dye precursors developer components which form the oxidation dyes by oxidative coupling with one another or with suitable coupler components. Suitable developer components useful in this invention include primary aromatic amines containing another free or substituted hydroxy or amino moiety in the para or othro position, diaminopyridine derivatives, heterocyclic hydrazones, 4-aminopyrazolone derivatives and 2,4,5,6-tetraaminopyrimidine and derivatives thereof. Suitable coupler components useful in this invention include m-phenylenediamine derivatives, napthols, resorcinol and resorcinol derivatives, pyrazolones and m-aminophenols. The couplers and developers, when present, are in oxidative hair dye effective amounts in relation to each other. The combined oxidative hair dye precursors, with the required oxidizing agent present in an oxidizing agent effective amount, may be present in any amount effective to alter the color of hair to be treated, to a desired degree.

To produce the hair dye preparations according to the invention, the first and optional second substantive hair dyes and the optional oxidation dye precursors, if any, are incorporated in suitable cosmetic carriers, such as creams, emulsions, gels, surfactant-containing foaming solutions such as shampoos, foam aerosols, or other preparations which are suitable for application to the hair.

Standard constituents of cosmetic preparations such as the above include: wetting agents and emulsifiers such as anionic, nonionic or ampholytic surfactants, preferably fatty alcohol sulfates, alkanesulfonates, alpha-olefin sulfonates, fatty alcohol polyglycol ether sulfates, ethlene oxide adducts with fatty alcohols, fatty acid adducts with alkylphenols, sorbitan fatty acid esters and fatty acid partial glycerides, and fatty acid alkanoloamides; thickeners such as methyl or hydroxyethyl cellulose, starch, fatty alcohols, paraffin oils, and fatty acids; and perfume oils and hair-care additives such as water soluble cationic polymers protein derivatives, panthothenic acid and cholesterol. The constituents of the cosmetic carriers are used in the usual quantities effective for preparing the hair dye preparations according to the invention. For example, emulsifiers are used in concentrations of 0.5 to 30% by weight and thickeners in concentrations of 0.1 to 25% by weight.

In the hair dye preparations according to the invention, the substantive hair dyes corresponding to general formula (I) preferably are used in a quantity of from 0.01 to 5.0% by weight, most preferably 0.1 to 2% by weight. In addition, known oxidation hair dye precursors (developer and coupler components, etc.) preferably are present in a combined quantity of from 0.01 to 5.0% by weight, most preferably 1.0 to 3.0% by weight.

If the hair dye preparation according to the invention contains oxidation dye precursors, it also is advisable to add a small quantity of a reducing agent, for example from 0.5 to 2.0% by weight of sodium sulfite, to stabilize the oxidation dye precursors. In this case, an oxidizing agent is added to the hair dye preparation before use in order to initiate oxidative development of the oxidation dye precursors. Oxidizing agents useful in this invention include, in particular, hydrogen peroxide or adducts thereof with urea, melamine or sodium borate as well as mixtures of these hydrogen peroxide adducts with potassium peroxysulfate. All of the above weights are based upon the weight of the hair dye preparation as a whole, it being understood that water is employed q.s. to 100%.

The hair dye preparations according to the invention may be used in a mildly acidic, neutral or alkaline medium, irrespective of the cosmetic carrier used, for example a cream, gel or shampoo. The hair dye preparations preferably have a pH range from 8 to 10. They may be used at temperatures of from 15 to 40° C. After a contact time of around 30 minutes, the hair dye preparation is removed by rinsing from the hair to be dyed. The hair may then be washed with a mild shampoo and dried. Washing with a shampoo is unnecessary when a carrier of high surfactant content, for example a dye shampoo, is used.

Hair dye finishes of high intensity, good fastness properties particularly to shampooing, and high stability to bleeding and changes in color during shampooing may be obtained with the hair dye preparations according to the invention. The following examples are intended to illustrate the invention without limiting it in any way.

EXAMPLES

Production Examples

1.
2,3'-dinitro-4'-aminodiphenylamine-4-carboxylic acid, sodium salt

A mixture of (A) 5.03 g (0.025 mol) 4-chloro-3-nitrobenzoic acid and (B) 3.82 g (0.025 mol) 2-nitro-p-phenylenediamine, 2.54 g (0.027 mol) sodium carbonate and 10 ml water was heated for 7 hours to 120° C. in an autoclave. After cooling, the solution was concentrated to dryness. The residue was recrystallized from a mixture of ethanol and water.

Yield: brown crystals, melting point above 350° C. (with decomposition)

2.
2,3'-dinitro-4'-aminodiphenylamine-4-sulfonic acid, sodium salt

Preparation was carried out in the same way as in Example 1 starting from
(A) 4-chloro-3-nitrobenzenesulfonic acid, sodium salt and
(B) 2-nitro-p-phenylenediamine.

Yield: brown crystals, melting point above 300° C.

3.
2,3'-dinitro-4'-(2-hydroxyethyl)-aminodiphenylamine-4-carboxylic acid Preparation was carried out in the same way as in Example 1 starting from
(A) 4-chloro-3-nitrobenzoic acid and
(B) 4-(2-hydroxyethyl)-amino-3-nitroaniline.

Yield: brown crystals, melting above 238° C. (with decomposition).

4.
2,3'-dinitro-4-(2-hydroxyethyl)-aminodiphenylamine-4-sulfonic acid, sodium salt Preparation was carried out in the same way as in Example 1 starting from
(A) 4-chloro-3-nitrobenzenesulfonic acid, sodium salt and (B) 4-(2-hydroxyethyl)-amino-3-nitroaniline.

Yield: light brown crystals, melting beyond 280° C. (with decomposition)

5.
3',4-dinitro-4'-(2-hydroxyethyl)-aminodiphenylamine-2-carboxylic acid, sodium salt Preparation was carried out in the same way as in Example 1 starting out from
(A) 2-chloro-5-nitrobenzoic acid and
(B) 4-(2-hydroxyethyl)-amino-3-nitroaniline.

Yield: dark brown crystals, melting point above 305° C.

6.
3',4-dinitro-6'-(2-hydroxyethyl)-aminodiphenylamine-2-carboxylic acid Preparation was carried out in the same way as in Example 1 starting out from
(A) 2-chloro-5-nitrobenzoic acid and
(B) 2-(2-hydroxyethyl)-amino-5-nitroaniline.

Yield: olive-brown crystals, melting point approx. 132° C. (with decomposition)

7.
3',4-dinitro-6'-aminophenylamine-2-carboxylic acid

Preparation was carried out in the same way as in Example 1 starting from
(A) 2-chloro-5-nitrobenzoic acid and
(B) 4-nitro-0-phenylenediamine.

Yield: orange-brown crystals, melting point 191-196° C.

8.
3',4-dinitro-4'-aminophenylamine-2-carboxylic acid

Preparation was carried out in the same way as in Example 1 starting from
(A) 2-chloro-5-nitrobenzoic acid and
(B) 2-nitro-p-phenylenediamine.

Yield: brown crystals, melting point above 310° C.

9.
3',4-dinitro-4-(2-hydroxyethyl)-aminodiphenylamine-2-sulfonic acid, sodium salt Preparation was carried out in the same way as in Example 1 starting from
(A) 2-chloro-5-nitrobenzenesulfonic aid, sodium salt and
(B) 4-(2-hydroxyethyl)-amino-3-nitroaniline.

Yield: brown crystals, melting point approx. 230° C. (with decomposition).

EXAMPLES 10 THROUGH 18
Hair dye tests

Hair dye creams were prepared from the following constituents:
$C_{12-18}$ fatty alcohol 10 g
$C_{12-14}$ fatty alcohol +2 EO sulfate, Na salt (28%) 25 g
Water 60 g
Substantive dye according to formula I 1 g
Ammonium sulfate 1 g
Concentrated ammonia solution to pH 9.5 g
Water q.s. ad 100 g The constituents were mixed together in the above order. After addition of the substantive dyes, the pH of the emulsion was first adjusted to 9.5 with concentrated ammonia solution, after which the emulsion was made up with water to 100 g.

The dye cream was applied to approx. 5 cm long strands of standardized, 90% grey, but not specially pretreated human hair and left thereon for 30 minutes at 27° C. After dyeing, the hair was rinsed, washed with a standard shampoo and then dried.

The compounds of Examples 1 to 9 were used as substantive hair dyes.

The results of the dyeing tests are shown in the table below.

TABLE
| | Results of hair dye tests | |
|---|---|---|
| Example | Substantive dye of Example no. | Color of the dyed hair |
| 10 | 1 | yellow-orange |
| 11 | 2 | mat yellow |
| 12 | 3 | beige |
| 13 | 4 | ivory |
| 14 | 5 | camel brown |
| 15 | 6 | brown-orange |
| 16 | 7 | yellow |
| 17 | 8 | yellow-orange |
| 18 | 9 | golden blond |

The above table indicates that hair colors obtained using the substantive dyes according to the invention are particularly desireable. When this is combined with the inventive dyes' excellent water dispersibility or solubility, the result is a very valuable product.

We claim:

1. In a hair dye aqueous preparation comprising a hair dye effective amount of a first substantive hair dye in a suitable cosmetic carrier, the improvement wherein said first substantive hair dye comprises one or more compounds of the formula:

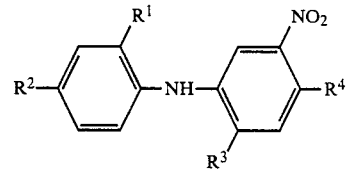

wherein:
one of $R^1$ or $R_2$ is nitro and the other is —$SO_3H$ or COOH; and
one of $R^3$ or $R_4$ is hydrogen and the other is —$NR^5R^6$, where $R^5$ and $R^6$ independently are hydrogen, $C_{1-4}$ alkyl, or $C_{2-4}$ hydroxyalkyl;
or a water soluble salt thereof.

2. The hair dye preparation of claim 1 wherein in the formula either $R^3$ or $R_4$ is amino or 2-hydroxyethylamino.

3. The hair dye preparation of claim 1 wherein said first substantive hair dye is a water soluble salt of sodium, potassium, ammonium, or a $C_{2-4}$ alkanolammonium.

4. The hair dye preparation of claim 2 wherein said first substantive hair dye is a water soluble salt of sodium, potassium, ammonium, or a $C_{2-4}$ alkanolammonium.

5. The hair dye preparation of claim 1 wherein said first substantive hair dye is 2,3'-dinitro-4'-aminodiphenylamine-4-carboxylic acid, sodium salt.

6. The hair dye preparation of claim 1 wherein said first substantive hair dye is 2,3'-dinitro-4'-aminodiphenylamine-4-sulfonic acid, sodium salt.

7. The hair dye preparation of claim 1 wherein said first substantive hair dye is 2,3'-dinitro-4'-(2-hydroxyethyl)-aminophenylamine-4-carboxylic acid.

8. The hair dye preparation of claim 1 wherein said first substantive hair is dye is 2,3'-dinitro-4-(2-hydroxyethyl)-aminodiphenylamine-4-sulfonic acid, sodium salt.

9. The hair dye preparation of claim 1 wherein said first substantive hair dye is 3',4-dinitro-4'-(2-hydroxyethyl)-aminodiphenylamine-2-carboxylic acid, sodium salt.

10. The hair dye preparation of claim 1 wherein said first substantive hair dye is 3',4-dinitro-6'-(2-hydroxyethyl)-aminodiphenylamine-2-carboxylic acid.

11. The hair dye preparation of claim 1 wherein said first substantive hair dye is 3',4-dinitro-6'-aminodiphenylamine-2-carboxylic acid.

12. The hair dye preparation of claim 1 wherein said first substantive hair dye is 3',4-dinitro-4'-aminodiphenylamine-2-carboxylic acid.

13. The hair dye preparation of claim 1 wherein said first substantive hair dye is 3',4-dinitro-4-(2-hydroxyethyl)-aminophenylamine-2-sulfonic acid, sodium salt.

14. The hair dye preparation of claim 1 in which said first substantive hair dye is present in about 0.01 to 5.0% by weight, based upon the weight of the hair preparation as a whole.

15. The hair dye preparation of claim 1 wherein one or more said second substantive hair dyes, one or more said oxidative hair dye precursors, or both, is present in an amount effective to alter the color of hair to be treated, to a desired degree.

16. The hair dye preparation of claim 1 wherein one or more said oxidative hair dye precursors are present in a combined quantity of about 0.01 to 5.0% by weight, based upon the weight of the hair dye preparation as a whole.

17. The hair dye preparation of claim 1, formulated as a cream, an emulsion, a gel, a shampoo, or an aerosol foam.

18. The hair dye preparation of claim 15, formulated as a cream, an emulsion, a gel, a shampoo, or an aerosol foam.

19. A nitrophenyldiamine derivative compound of the formula

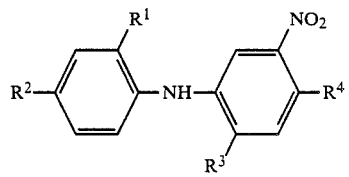

wherein:
one of $R^1$ or $R^2$ is nitro and the other is —$SO_3H$ or COOH; and
one of $R^3$ or $R^4$ is hydrogen and the other is —$NR_5R^6$, where $R^5$ and $R^6$ independently are hydrogen, $C_{1-4}$ alkyl, or $C_{2-4}$ hydroxalkyl;
or a water soluble salt thereof.

20. The compound of claim 19 having the formula: 2,3'-dinitro-4'-aminodiphenylamine-4-carboxylic acid, sodium salt.

21. The compound of claim 19 having the formula: 2,3'-dinitro-4'-aminodiphenylamine-4-sulfonic acid, sodium salt.

22. The compound of claim 19 having the formula: 2,3'-dinitro-(2-hydroxyethyl)-aminodiphenylamino-4-carboxylic acid.

23. The compound of claim 19 having the formula: 2,3'-dinitro-4-(2-hydroxyethyl)-aminodiphenylamine-4-sulfonic acid, sodium salt.

24. The compound of claim 19 having the formula: 3',4-dinitro-4'-(2-hydroxyethyl)-aminodiphenylamine-2-carboxylic acid, sodium salt.

25. The compound of claim 19 having the formula: 3',4-dinitro-6'-(2-hydroxyethyl)-aminodiphenylamine-2-carboxylic acid, sodium salt.

26. The compound of claim 19 having the formula: 3'-4-dinitro-6'-aminodiphenylamine-2-carboxylic acid.

27. The compound of claim 19 having the formula:
pb   3'-4-dinitro-4'-aminodiphenylamine-2-carboxylic acid.

28. The compound of claim 19 having the formula: 3,4'-dinitro-4-(2-hydroxyethyl)-aminodiphenylamine-2-sulfonic acid, sodium salt.

29. A method for dyeing hair comprising
applying to the hair a hair-dyeing effective amount of the preparation of claim 1;
permitting said preparation to remain on said hair for a hair-dyeing effective time; and
removing free hair dye from said hair.

* * * * *